United States Patent
Shinka et al.

(10) Patent No.: US 8,987,522 B2
(45) Date of Patent: *Mar. 24, 2015

(54) DIFFERENTIATION INDUCER TO BROWN-LIKE ADIPOCYTE OF WHITE ADIPOCYTE

(71) Applicant: Uha Mikakuto Co., Ltd., Yamatokooriyama-shi (JP)

(72) Inventors: Yasuhiro Shinka, Yamatokooriyama (JP); Akinobu Kishi, Yamatokooriyama (JP); Taiji Matsukawa, Yamatokooriyama (JP); Takeki Matsui, Yamatokooriyama (JP); Yasumasa Yamada, Yamatokooriyama (JP); Ichiro Yamada, Yamatokooriyama (JP)

(73) Assignee: Uha Mikakuto Co., Ltd., Yamatokooriyama-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/108,909

(22) Filed: Dec. 17, 2013

(65) Prior Publication Data
US 2014/0171690 A1 Jun. 19, 2014

(30) Foreign Application Priority Data
Dec. 17, 2012 (JP) .................. 2012-275026

(51) Int. Cl.
*C07C 43/205* (2006.01)
*C07C 39/21* (2006.01)
*C12N 5/077* (2010.01)

(52) U.S. Cl.
CPC ........ *C12N 5/0653* (2013.01); *C12N 2501/999* (2013.01)
USPC ....................................... 568/640

(58) Field of Classification Search
None
See application file for complete search history.

(56) References Cited

U.S. PATENT DOCUMENTS

2013/0296613 A1* 11/2013 Kishi et al. .................. 568/641

FOREIGN PATENT DOCUMENTS

| JP | 2010-24208 A1 | 2/2010 |
| JP | 2011-241195 A1 | 12/2011 |
| JP | 2012-246243 A1 | 12/2012 |

OTHER PUBLICATIONS

X. Yao, et al.; "Recent progress in the study of brown adipose tissue;" Cell & Bioscience; 1:35; 2011; pp. 1-9 (9 sheets total)/p. 4 of specification.
J. Wu, et al.; "Beige Adipocytes Are a Distinct Type of Thermogenic Fat Cell in Mouse and Human;" Cell; vol. 150; Jul. 20, 2012; pp. 366-376 (11 Sheets total)/p. 4 of specification.
H. Ohno, et al.; "PPARgamma agonists Induce a White-to-Brown Fat Conversion through Stabilization of PRDM16 Protein;" Cell Metabolism; vol. 15; Mar. 7, 2012; pp. 395-404 (10 sheets total)/p. 4 of specification.
Basic and Applied Sciences of Resveratrol; CMC Publishing Co., Ltd.; Sep. 20, 2012; cover sheets, index, and endsheets (12 sheets total)/p. 4 of specification.
F. Picard, et al.; "Sirt1 promotes fat mobilization in white adipocytes by repressing PPAR-gamma;" Nature; vol. 429 (6993); Jun. 17, 2004; pp. 1-14 (14 sheets total)/p. 4 of specification.
J. Mattison, et al.; "Impact of caloric restriction on health and survival in rhesus monkeys from the NIA study;" Nature; vol. 489; Sep. 13, 2012; pp. 318-321 (4 sheets)/p. 4 of specification.

* cited by examiner

*Primary Examiner* — Brian J Davis
(74) *Attorney, Agent, or Firm* — Kratz, Quintos & Hanson, LLP

(57) ABSTRACT

A differentiation inducer to brown-like adipocytes of white adipocytes containing a novel compound having an excellent differentiation induction action to brown-like adipocytes of white adipocytes as compared with resveratrol. A differentiation inducer to brown-like adipocytes of white adipocytes which is a reaction product of hydroxystilbenes and sinapic acid and contains a compound represented by Formula (1) or a pharmacologically permissible salt thereof:

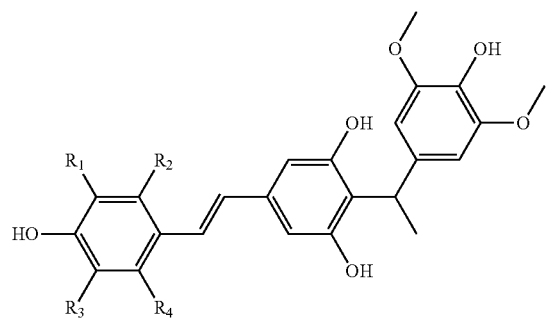

Formula (1)

in which, in Formula (1),
$R_1$ to $R_4$ represents a hydrogen atom, a hydroxy group, a saturated or unsaturated, linear or branched alkoxy group having 1 to 10 carbon atoms, or a saturated or unsaturated, linear or branched alkyl group having 1 to 10 carbon atoms and $R_1$ to $R_4$ each may be the same or different.

1 Claim, 2 Drawing Sheets
(2 of 2 Drawing Sheet(s) Filed in Color)

DIFFERENTIATION INDUCER TO BROWN-LIKE ADIPOCYTE OF WHITE ADIPOCYTE

BACKGROUND OF THE INVENTION

1. Field of the Invention

The present invention relates to a differentiation inducer to brown-like adipocytes of white adipocytes, the differentiation inducer which contains a reaction product of hydroxystilbenes and sinapic acid obtained by a synthesis method which is a very simple method and is applicable also to foods.

2. Description of the Background Art

Adipocytes constituting the adipose tissue of mammals include two kinds of adipocytes, white adipocytes and brown adipocytes. The white adipocytes mainly have a role of accumulating the chemical energy taken in the form of triglyceride. On the other hand, the brown adipocytes have a role of converting the accumulated energy to heat. The brown adipocytes generate from myoblasts and are colored brown due to a large number of mitochondria contained in the cells. The brown adipocytes generate heat by the action of Uncoupling protein 1 (UCP1) expressed in the mitochondria (Non-patent Literature 1).

A large amount of the brown adipose tissue constituted by the brown adipocytes can be seen in human infant, but the presence of brown fat in the tissue decreases with growth. It has been considered that since the derived stem cells are different, the brown adipocytes are not expressed from the white adipocytes. In recent years, however, the existence of "brown-like adipocytes" which show the same response as that of the brown adipocytes in the white adipose tissue has been clarified (Non-patent Literature 2). Although the brown-like adipocytes are derived from the white adipocytes, the amount of mitochondria in the brown-like adipocytes is markedly large as compared with that of the white adipocytes and the accumulated lipid energy is efficiently converted to heat energy. Therefore, the differentiation induction of the white adipocytes to the brown-like adipocytes has drawn attention as a fundamental medical treatment method of obesity or diabetes.

However, it is difficult to induce the differentiation of the white adipocytes to the brown-like adipocytes. Confirmed methods are only prolonged cold stimulation, stimulus by adrenalin (Non-Patent Literature 1), addition of peroxisome proliferator-activated receptor (PPARγ) agonist (Non-Patent Literature 3), and the like. In addition, in all the methods above, the differentiation induction effect is limited only in subcutaneous adipocytes. These methods do not have an effect to the mouse-derived preadipocyte 3T3-L1 as the model cell of the white adipocytes and the visceral adipose which is the cause of the metabolic syndrome typified by obesity and diabetes. Moreover, although a compound having an expression amplification effect of the UCP1 gene to the human visceral adipocytes has been reported in Patent Literature 1, the working concentration is very high, so that it is difficult to achieve the effective concentration in the living body and bronzing of the white adipocytes is not referred to.

On the other hand, it is supposed that the useful physiological effect of red wine referred to as so-called "French paradox" is caused by various kinds of bioactive functions including the anti-oxidization ability of resveratrol. The resveratrol is one of the hydroxystilbenes mostly contained in grape pericarp and peanut red bark. The resveratrol is known to be a plant-derived compound having a calorie restriction effect through sirtuin and various activities, such as an antifungal effect, an antibacterial effect, and an anti-inflammation effect (Non-Patent Literature 4). Furthermore, it has been reported that the resveratrol has action of differentiation to adipocytes through the expression promotion of sirtuin and suppression of the accumulation of fat (Non-Patent Literature 5). However, under the circumstances where there arises a doubt as a result of an experiment to Macacus rhesus as to where the calorie restriction itself has an effect useful for life extension (Non-Patent Literature 6), the calorie restriction effect through sirtuin to human beings of the resveratrol is not also certain. Moreover, although it has been reported that the resveratrol has a gene expression enhancement effect of Uncoupling protein UCP2 specifically expressed in the white adipocytes (Patent Literature 2), the differentiation effect from the white adipocytes to the brown-like adipocytes of the resveratrol has not been referred to at all so far.

The sinapic acid is known to be one of secondary metabolites of plants, a component mostly present in the plant kingdom as precursors of lignin and lignan as the main component of trees, and mostly contained in fruits, such as apples, grains, such as wheat, and the cruciferous plant, such as broccoli sprout. An anti-oxidization effect of the sinapic acid and derivatives thereof is known but an effect of differentiation to the brown-like adipocytes from the white adipocytes thereof is not known at all.

Thus, a development of fundamental medical treatment and prevention agents which prevent and medically treat the metabolic syndrome, not by suppression of appetite or suppression of fat absorption, but by changing the properties of the adipocytes themselves to change metabolism and functional foods containing the agents has been desired until today. However, a substance which is admitted to have a sufficient effect to all the white adipocytes has not been found so far, and an early development thereof has been desired.

CITATION LIST

Patent Literature

Patent Literature 1: Japanese Unexamined Patent Application Publication No. 2011-241195
Patent Literature 2: Japanese Unexamined Patent Application Publication No. 2010-24208
Patent Literature 3: Japanese Unexamined Patent Application Publication No. 2012-246243

Non-Patent Literature

Non-Patent Literature 1: Cell Biosci. 2011 Oct. 28; 1:35
Non-Patent Literature 2: Cell. 2012, July 20; 150(2):366-769
Non-Patent Literature 3: Cell Metab. 2012 Mar. 7; 15(3):395-404
Non-Patent Literature 4: Basis and Application of Resveratrol, CMC Publishing Co., Ltd.
Non-Patent Literature 5: Nature. 2004 Jun. 17; 429(6993): 771
Non-Patent Literature 6: Nature. 2012 Sep. 13; 489(7415): 318

SUMMARY OF THE INVENTION

The present inventors have conducted extensive researches for searching a compound showing the differentiation induction action to brown-like adipocytes of white adipocytes and achieving a method for manufacturing the compound in view of the above-described circumstances. As a result, the present inventors have unexpectedly succeeded in manufacturing a novel compound showing the differentiation induction action to brown-like adipocytes of white adipocytes by a simple and safe method of heating hydroxystilbenes and sinapic acid in the presence of a metal salt, and have accomplished the present invention. Therefore, it is an object of the present invention to provide a differentiation inducer to brown-like adipocytes of white adipocytes containing a novel compound having an excellent differentiation induction action to brown-like adipocytes of white adipocytes as compared with resveratrol.

Means to Solve the Problems

More specifically, the scope of the present invention relates to a differentiation inducer to brown-like adipocytes of white adipocytes which is a reaction product of hydroxystilbenes and sinapic acid and contains a compound represented by Formula (1) or a pharmacologically permissible salt thereof.

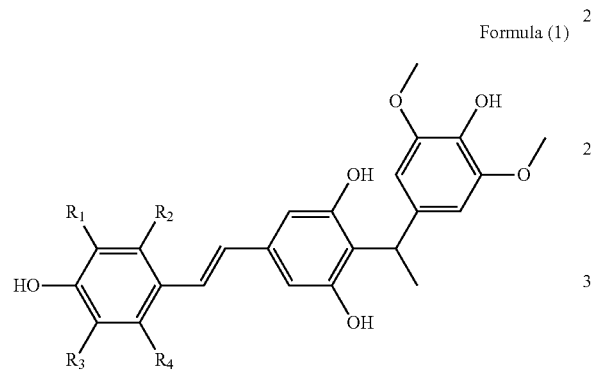

Formula (1)

In Formula (1), $R_1$ to $R_4$ represents a hydrogen atom, a hydroxy group, a saturated or unsaturated, linear or branched alkoxy group having 1 to 10 carbon atoms, or a saturated or unsaturated, linear or branched alkyl group having 1 to 10 carbon atoms and $R_1$ to $R_4$ each may be the same or different.

Effects of the Invention

The compound represented by Formula (1) above or a pharmacologically permissible salt thereof to be used in the present invention has a remarkably excellent differentiation induction action to brown-like adipocytes from white adipocytes as compared with hydroxystilbenes as a precursor and is useful as a novel metabolic syndrome medical treatment and prevention substance. Moreover, since the differentiation induction action to brown-like adipocytes from white adipocytes of the compound represented by Formula (1) above or a pharmacologically permissible salt is not observed in sinapic acid or a salt thereof as the other precursor, the differentiation induction action can be said to be a prominent effect.

By compounding the differentiation inducer to brown-like adipocytes from white adipocytes of the present invention in foods, pharmaceutical drugs, or quasi drugs, novel metabolic syndrome preventing or improving foods, pharmaceutical drugs, or quasi drugs can be provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODES FOR CARRYING OUT THE INVENTION

Figure 1:
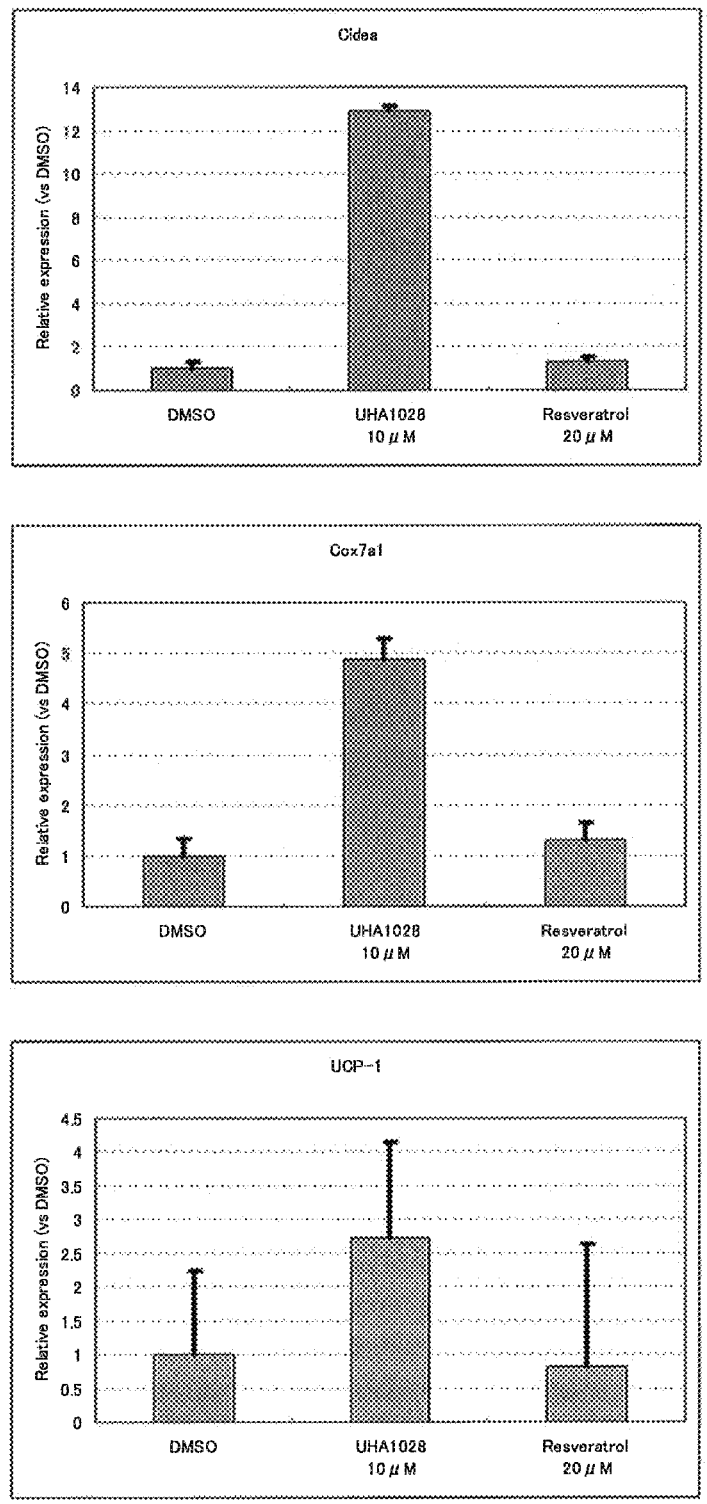
FIG. 1 is a graph showing the relative expression amount of each of a Cell death-inducing DFFA-like effector a (Cidea) which is a brown-like adipocyte marker gene, a cytochrome c oxidase polypeptide 7A1 (Cox7a1) which is a mitochondria marker gene, and a UCP1 gene in adipocytes after differentiation induction carried out in Example 2.

Hereinafter, the present invention is described in detail.

A reaction product of hydroxystilbenes and sinapic acid to be used in the invention is a compound represented by Formula (1) or a pharmacologically permissible salt thereof.

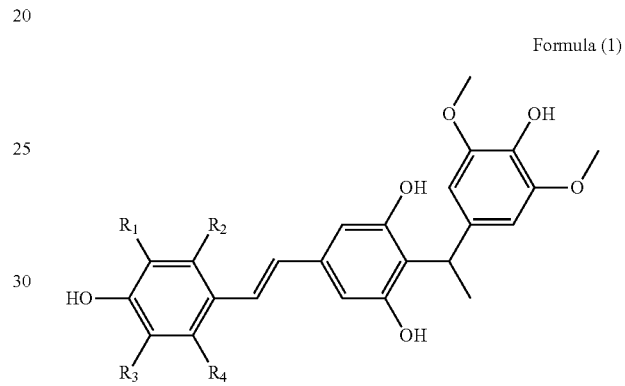

Formula (1)

In Formula (1), $R_1$ to $R_4$ represents a hydrogen atom, a hydroxy group, a saturated or unsaturated, linear or branched alkoxy group having 1 to 10 carbon atoms, or a saturated or unsaturated, linear or branched alkyl group having 1 to 10 carbon atoms and $R_1$ to $R_4$ each may be the same or different.

In Formula (1) above, although the saturated or unsaturated, linear or branched alkoxy group having 1 to 10 carbon atoms represented by $R_1$ to $R_4$ is not particularly limited and is preferably a linear or branched alkoxy group having 1 to 4 carbon atoms. Mentioned as a specific example thereof are a methoxy group, an ethoxy group, an n-propoxy group, an isopropoxy group, an n-butoxy group, an isobutoxy group, an s-butoxy group, a t-butoxy group, and the like.

The saturated or unsaturated, linear or branched alkyl group having 1 to 10 carbon atoms represented by $R_1$ to $R_4$ is not particularly limited and is preferably a linear or branched alkyl group having 1 to 5 carbon atoms. Mentioned as a specific example thereof are a methyl group having 1 to 5 carbon atoms, an ethyl group, n-propyl group, an isopropyl group, an n-butyl group, an isobutyl group, an s-butyl group, a t-butyl group, an n-pentyl group, an isopentyl group, a t-pentyl group, a neopentyl group, and the like.

Among the above, it is preferable that one or more of $R_1$ to $R_4$ above are hydrogen atoms and it is more preferable that all of $R_1$ to $R_4$ above are hydrogen atoms.

In the compound represented by Formula (1) above, a carbon-carbon double bond may be trans or cis. The compound represented by Formula (1) above may be a mixture of a cis-isomer and a trans isomer.

Mentioned as the pharmacologically permissible salt of the compound represented by Formula (1) above are, for example, alkali metal salts, such as lithium salt, sodium salt, and potassium salt; alkaline earth metal salts, such as magnesium salt, calcium salt, and barium salt; aluminum salt; metal hydroxide salts, such as aluminum hydroxide salt; amine salts, such alkyl amine salt, dialkyl amine salt, trialkyl amine salt, alkylene diamine salt, cycloalkyl amine salt, aryl amine salt, aralkyl amine salt, and heterocyclic amine salt; amino acid salts, such as α-amino acid salt and ω-amino acid salt; peptide salt or primary amine salt, secondary amine salt, tertiary mine salt, or quaternary amine salt derived therefrom, and the like. These pharmacologically permissible salts can be used singly or as a mixture of two or more kinds.

The compound represented by Formula (1) above or the pharmacologically permissible salt thereof (hereinafter also referred to as the compound represented by Formula (1) above) has action of inducing differentiation of white adipocytes to brown-like adipocytes. The adipocyte differentiation induction action can be specifically measured by a method described in Example 2 described later.

The compound represented by Formula (1) above is obtained by heating hydroxystilbenes and sinapic acid as a raw material compound in the presence of metal salt.

The hydroxystilbenes are hydroxystilbene derivatives represented by Formula (2) and pharmacologically permissible salts thereof:

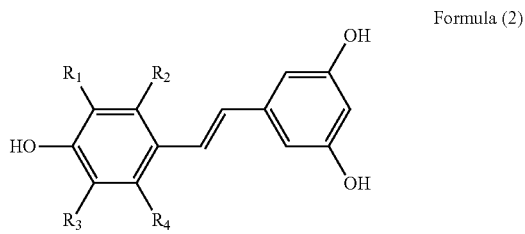

Formula (2)

In Formula (2), $R_1$ to $R_4$ represents a hydrogen atom, a hydroxy group, a saturated or unsaturated, linear or branched alkoxy group having 1 to 10 carbon atoms, or a saturated or unsaturated, linear or branched alkyl group having 1 to 10 carbon atoms and $R_1$ to $R_4$ each may be the same or different.

In Formula (2) above, although the saturated or unsaturated, linear or branched alkoxy group having 1 to 10 carbon atoms represented by $R_1$ to $R_4$ is not particularly limited and is preferably a linear or branched alkoxy group having 1 to 4 carbon atoms. Mentioned as a specific example thereof are a methoxy group, an ethoxy group, an n-propoxy group, an isopropoxy group, an n-butoxy group, an isobutoxy group, an s-butoxy group, a t-butoxy group, and the like.

The saturated or unsaturated, linear or branched alkyl group having 1 to 10 carbon atoms represented by $R_1$ to $R_4$ is not particularly limited and is preferably a linear or branched alkyl group having 1 to 5 carbon atoms. Mentioned as a specific example thereof are a methyl group having 1 to 5 carbon atoms, an ethyl group, n-propyl group, an isopropyl group, an n-butyl group, an isobutyl group, an s-butyl group, a t-butyl group, an n-pentyl group, an isopentyl group, a t-pentyl group, a neopentyl group, and the like. Among the above, it is preferable that one or more of $R_1$ to $R_4$ above are hydrogen atoms and it is more preferable that all of $R_1$ to $R_4$ above are resveratrol.

Mentioned as the pharmacologically permissible salt of the compound represented by Formula (2) above are, for example, alkali metal salts, such as lithium salt, sodium salt, and potassium salt; alkaline earth metal salts, such as magnesium salt, calcium salt, and barium salt; aluminum salt; metal hydroxide salts, such as aluminum hydroxide salt; amine salts, such alkyl amine salt, dialkyl amine salt, trialkyl amine salt, alkylene diamine salt, cycloalkyl amine salt, aryl amine salt, aralkyl amine salt, and heterocyclic amine salt; amino acid salts, such as α-amino acid salt and ω-amino acid salt; peptide salt or primary amine salt, secondary amine salt, tertiary mine salt, or quaternary amine salt derived therefrom, and the like. These pharmacologically permissible salts can be used singly or as a mixture of two or more kinds.

The hydroxystilbenes to be used as the raw material compound may be a naturally derived one or a chemical product with high purity which is chemically synthesized. The naturally-derived material compound does not need to be completely refined and a mixture containing each raw material compound can also be used.

From the viewpoint of increasing the generation efficiency and the recovery rate of the compound represented by Formula (1) above, one containing the hydroxystilbenes in a total proportion of 5% by weight or more as the hydroxystilbenes is preferable as the raw material. As such raw materials, extracts from raw materials, such as grape pericarp, peanut pericarp, and Japanese knotweed, freeze-dried products of the extracts, and the like may be used, for example.

The sinapic acid to be used as a raw material compound may be a naturally-derived one or a chemical product with high purity which is chemically synthesized. When naturally-derived sinapic acid is used, a completely refined one does not need to use and a mixture containing ingredients other than the sinapic acid can also be used insofar as a desired generation reaction progresses, so that the compound represented by Formula (1) above is obtained as described later.

As the sinapic acid, pharmacologically permissible salts are also mentioned. As a specific example thereof, salts, such as sodium salt, potassium salt, and calcium salt, are mentioned. From the viewpoint of increasing the generation efficiency and the recovery amount of the compound represented by Formula (1), one containing the sinapic acid in a proportion of 5% by weight or more is preferable as the raw material. As such raw materials, extracts from raw materials, such as apple fruit and oilseed rape, freeze-dried products thereof, and the like are mentioned, for example.

In the present invention, a mixture of the hydroxystilbenes and the sinapic acid is dissolved in a suitable solvent. In this case, when the solvent contains only water, the solubility in water of both the hydroxystilbenes and the sinapic acid is low. Therefore, the mixture is preferably dissolved in a mixed liquid of water and an organic solvent or only an organic solvent. The compounding ratio of water and the organic solvent and the type of the organic solvent are not particularly limited, and the hydroxystilbenes and the sinapic acid may be sufficiently dissolved. In particular, it is preferable in terms of the safety and the cost to use a solvent containing only methanol or only ethanol, a mixed liquid of water and methanol, a mixed liquid of water and ethanol, and the like. When using the composition, which is obtained after the generation reaction, without being sufficiently subjected to final refining for foods, pharmaceutical drugs, quasi drugs, and the like, it is desirable to use ethanol, water, or hydrous ethanol as a solvent in terms of safety or laws and regulations.

The concentration of the hydroxystilbenes and the sinapic acid in a mixed solution obtained by dissolving the hydroxystilbenes and the sinapic acid in a solvent as described above is not particularly limited. There are merits, e.g., when the concentration of each of the hydroxystilbenes and the sinapic acid is higher, the use amount of the solvent is smaller. Therefore, it is suitable to adjust the concentration of the hydroxystilbenes and the concentration of the sinapic acid to be close to a concentration at which the hydroxystilbenes and the sinapic acid are saturated in the solvents thereof.

The hydroxystilbenes and the sinapic acid do not need to be completely dissolved before the generation reaction in the mixed solution. For example, a case where a solution containing the hydroxystilbenes and a solution containing the sinapic acid are mixed is described. Even when both the concentration of the hydroxystilbenes and the concentration of the sinapic acid in the solutions thereof are equal to or higher than the saturated concentration, the concentration of the hydroxystilbenes and the concentration of the sinapic acid may be adjusted to be close to the saturated concentration in the case of a mixed solution thereof.

Next, it is preferable to adjust the pH of the mixed solution containing the hydroxystilbenes and the sinapic acid (hereinafter also referred to as a solution containing the hydroxystilbenes and the sinapic acid) to lower than 8. As adjustment methods, the solution containing the hydroxystilbenes and the sinapic acid is prepared, and then a pH adjuster may be added to adjust the pH or the pH of a solvent may be adjusted beforehand in the preparation of the solution, for example. When the pH when starting the reaction of the solution containing the hydroxystilbenes and the sinapic acid is 8.0 or higher, another reaction or decomposition of the target compound occurs. Therefore, the recovery amount of the compound represented by Formula (1) tends to decrease. Therefore, the pH when starting the reaction of the solution containing the hydroxystilbenes and the sinapic acid is desirably 3 or higher and lower than 8.

In the present invention, in order to obtain the target compound represented by Formula (1) by reacting the hydroxystilbenes and the sinapic acid as the raw material compound, metal salt is added to the solution containing the hydroxystilbenes and the sinapic acid.

The metal salt may be any one of acidic salts, basic salts, and normal salts and may be any one of single salts, double salts, and complex salts. The metal salt may be one kind of metal salt or a mixture of two or more kinds of metal salts. As an example of the metal salt, one which is approved as a food additive is preferable in terms of safety. For example, magnesium salt, calcium salt, sodium salt, potassium salt, zinc salt, copper salt, and the like which are allowed to be added to foods are mentioned.

As a mixture of the metal salts, a mixture containing several kinds of metal salts, such as mineral premix (manufactured by Mitsubishi Tanabe Pharma Corporation), Mineral mixture containing zinc gluconate, iron ammonium citrate, calcium lactate, copper gluconate, and magnesium phosphate as the main component) is mentioned, for example. Moreover, mineral water can also be mentioned as a mixture containing two or more metal salts.

The content of the metal salts in the solution containing the hydroxystilbenes and the sinapic acid is not particularly limited insofar as the target compound represented by Formula (1) can be generated.

The reaction of generating the compound represented by Formula (1) progresses in the presence of the metal salt. The generation reaction further progresses under the conditions of a pH of 3 or higher and lower than 8.

It is preferable to select the reaction conditions as appropriate considering the intended use of the compound represented by Formula (1) to be obtained, presence of refining and isolating operation, taste when adding the same to foods, and the like.

Next, by heating the solution containing the hydroxystilbenes and the sinapic acid to which the metal salt is added, the hydroxystilbenes and the sinapic acid are heat treated in the presence of the metal salt. This heat treatment causes the generation reaction of the compound represented by Formula (1) above. In order to let the generation reaction efficiently progress, the heating temperature is preferably adjusted to 90° C. or higher. Considering the boiling point of a solvent for use in the solution containing the hydroxystilbenes and the sinapic acid, heating under pressurization is desirably performed. For example, the solution containing the hydroxystilbenes and the sinapic acid to which the metal salt is added is put in an open container, the container is heated at a high temperature exceeding the boiling point of the solvent, the solution containing the hydroxystilbenes and the sinapic acid to which the metal salt is added is put in an airtight container, and then the container is heated. The heating is preferably performed in such a manner that the solution temperature at least partially reaches 110° C. or higher by, for example, heating under pressurization using a retort device or an autoclave. It is more preferable that the solution temperature uniformly becomes 110° C. to 150° C. in terms of increasing the generation efficiency and the recovery efficiency of the compound represented by Formula (1) above. The heating time is not limited similarly to the case of the heating temperature and the time conditions may be determined in such a manner that the target reaction efficiently progresses. In particular, the heating time depends on the balance of the heating temperature and the solvent amount and the heating time is desirably determined according to the heating temperature and the solvent amount. For example, when heating the solution containing the hydroxystilbenes and the sinapic acid to which the metal salt is added around 130° C., it is preferable to perform the heating for 5 minutes to 6 hours after the solution temperature reaches 130° C. The heating may be performed once or repeatedly performed while dividing the heating process into a plurality of processes. When heating the solution containing the hydroxystilbenes and the sinapic acid to which the metal salt is added while dividing the addition process into a plurality of processes, it is preferable to perform the heating while adding another solvent alone or another solvent containing metal salt.

The end of the generation reaction of the compound represented by Formula (1) above by the heat treatment may be judged by confirming the generation amount of the compound represented by Formula (1) by componential analysis by HPLC described in Examples described later, for example.

When the compound represented by Formula (1) above is manufactured by a process using only safe materials, the compound represented by Formula (1) above can be used in the form of a mixture containing the compound represented by Formula (1) above for foods, pharmaceutical drugs, quasi drugs, and the like as described later. For example, when a naturally-derived raw material compound is dissolved in a hydrous ethanol solvent, and then heat-treated using mineral water or mineral premix, it is possible to use the liquefied reactant to be obtained as one of the raw materials of foods, pharmaceutical drugs, quasi drugs, and the like.

When an improvement of flavor and a higher functionality are desired, a pure product of the compound represented by Formula (1) can be obtained by concentrating the reactant to increase the concentration of the compound represented by Formula (1) or refining the reactant. The concentration and the refining can be carried out by known methods. For example, the compound represented by Formula (1) can be concentrated by extracting by a solvent extraction method using chloroform, ethyl acetate, ethanol, methanol, or the like, a supercritical extraction method with carbon dioxide, or the like. It is also possible to perform concentration and refining utilizing column chromatography. For the concentration and the refining, a recrystallization method and a membrane process using an ultrafiltration membrane or the like can also be used.

When separating the compound represented by Formula (1) above from the reactant and collecting the same, column chromatography, HPLC, and the like may be used.

By drying under reduced pressure or freeze-drying the concentrate or the refined substance as required for removing the solvent, a powdery solid can be obtained.

The compound represented by Formula (1) obtained as described above has a stronger action of inducing the differentiation to brown-like adipocytes from white adipocytes as compared with the hydroxystilbenes as the raw material. Due to the differentiation induction action to brown-like adipocytes, prevention and improvement of metabolic syndrome can be achieved. Therefore, a pharmaceutical drug of the present invention containing the compound represented by Formula (1) as an active ingredient is useful as a novel prevention agent and/or medical treatment agent of metabolic syndrome. The action of inducing the differentiation to brown-like adipocytes from white adipocytes is an action which is not observed in the hydroxystilbenes and the sinapic acid as the raw material.

The differentiation inducer to brown-like adipocytes of white adipocytes of the present invention may contain only the compound represented by Formula (1) above or may be prepared into a liquid agent in which the compound represented by Formula (1) above is dissolved in a solvent, such as ethanol or an aqueous ethanol containing solution, or prepared into an emulsion or a suspension by known methods. The content of the compound represented by Formula (1) above in the differentiation inducer to brown-like adipocytes of white adipocytes of the present invention may be 0.001% by weight or more.

The dose amount of the differentiation inducer to brown-like adipocytes of white adipocytes of the present invention can be selected from a wide range of dose amounts as appropriate according to the sex, age, physiological state, and pathology (progress of obesity and the like) of patients, the agent form, the administration route, the administration frequency, the active ingredient concentration of pharmaceutical drugs, and the like. For example, the content of the compound represented by Formula (1) of one adult may be about 0.01 to 500 mg/kg and preferably about 0.1 to 100 mg/kg per day. The administration may be performed one time or divided into several times per day, for example.

The differentiation inducer to brown-like adipocytes of white adipocytes of the present invention may be prepared into an agent as a pharmaceutical drug. The agent form is not particularly limited and, for example, parenteral forms such as injections, suppositories, ophthalmic solutions, ointments, and aerosols, and oral forms such as tablets, coated tablets, powders, fine grains, granules, capsules, fluids, pills, suspensions, emulsions, troches, chewable tablets, and syrups, and the like are mentioned. When prepared into agents, pharmacologically permissible carriers, excipients, lubricants, binders, disintegrators, diluents, stabilizers, isotonizing agents, pH adjusters, buffers, and the like are used.

Mentioned as the carriers or the diluents are, for example, lactose, sucrose, sodium chloride, grape sugar, maltose, mannitol, erythritol, xylitol, maltitol, inositol, dextran, sorbitol, albumin, urea, starch, calcium carbonate, kaolin, microcrystalline cellulose, silicic acid, methyl cellulose, glycerin, sodium alginate, gum arabic, mixtures thereof, and the like.

Mentioned as the lubricants are, for example, refined talc, stearic acid salt, borax, polyethylene glycol, mixtures thereof, and the like.

Mentioned as the binders are, for example, simple syrup, grape sugar liquid, starch liquid, gelatin solution, polyvinyl alcohol, polyvinyl ether, polyvinyl pyrrolidone, carboxymethyl cellulose, shellac, methyl cellulose, ethyl cellulose, water, ethanol, potassium phosphate, mixtures thereof, and the like.

Mentioned as the disintegrators are, for example dry starch, sodium alginate, agar powder, laminaran powder, sodium bicarbonate, calcium carbonate, polyoxyethylene sorbitan fatty acid esters, sodium lauryl sulfate, monoglyceride stearate, starch, lactose, mixtures thereof, and the like.

Mentioned as the diluentes are, for example, water, ethyl alcohol, macrogol, propylene glycol, ethoxized isostearyl alcohol, polyoxidized isostearyl alcohol, and polyoxyethylene sorbitan fatty acid esters, mixtures thereof, and the like.

Mentioned as the stabilizers are, for example, sodium pyrosulfite, ethylenediaminetetraacetate, thioglycolic acid, thiolactic acid, mixtures thereof, and the like.

Mentioned as the isotonizing agents are, for example, sodium chloride, boric acid, grape sugar, glycerin, mixtures thereof, and the like.

Mentioned as the pH adjusters and buffer are, for example, sodium citrate, citric acid, sodium acetate, sodium phosphate, mixtures thereof, and the like.

The differentiation inducer to brown-like adipocytes of white adipocytes of the present invention may contain extenders, solubilizing agents, dispersants, suspensions, emulsifiers, antioxidization agents, microbial inhibitors, colorants, taste improving agents, odor improving agents, and the like.

The differentiation inducer to brown-like adipocytes of white adipocytes of the present invention may be prepared into the form of foods. The foods are not particularly limited and, for example, beverages, alcoholic beverages, jellies, confectioneries, functional foods, health foods, health oriented foods, and the like are mentioned. Considering storageability, portability, ease of ingestion, and the like, confectioneries are preferable and, among confectioneries, hard candies, soft candies, gummi candies, tablets, chewing gums, and the like are preferable.

When the differentiation inducer to brown-like adipocytes of white adipocytes of the present invention is prepared into the form of foods, the content in the foods of the compound represented by Formula (1) is usually about 0.001 to 20% by weight.

The differentiation inducer to brown-like adipocytes of white adipocytes of the present invention may be prepared into the form of quasi drugs. The quasi drugs are not particularly limited, and nutrition supplement quasi drugs, such as health drink, are preferable, for example. In this case, the content in the quasi drugs of the compound represented by Formula (1) which is an active ingredient is usually about 0.001 to 30% by weight.

The differentiation inducer to brown-like adipocytes of white adipocytes of the present invention is not only for human beings and may be blended in medical treatment agents or feed for non-human animals, e.g., mammals, such as rats, mice, guinea pigs, rabbits, sheep, pigs, cows, horses, cats, dogs, apes, and chimpanzees, birds, amphibians, and reptiles. Mentioned as the feed are a feed for livestock for sheep, pigs, horses, cows, chickens, and the like, a feed for small animals, such as rabbits, rats, and mice, a feed for fish and shellfish, such as eels, sea breams, yellowtails, and shrimps, and a pet food for dogs, cats, little birds, and squirrels.

Next, the present invention is described in detail with reference to Examples but is not limited only to the Examples. Herein, although trans-resveratrol is used as hydroxystilbenes, a compound is obtained by the same reaction even in the case of other hydroxystilbenes.

EXAMPLES

Example 1

Generation and Isolation and Refining of UHA1028

1 g of trans-resveratrol and 1 g of sinapic acid (manufactured by Wako Pure Chemical Industries, Ltd.) were dissolved in 20 mL of ethanol, and then 20 mL of mineral water was added, thereby obtaining a solution containing the resveratrol and the sinapic acid (pH=4.9). The solution containing the resveratrol and the sinapic acid was heated at 130° C. for 90 minutes in an autoclave ("SANYO LABO AUTOCLAVE", manufactured by SANYO Electric Co., Ltd.). 1 mL of the obtained reaction solution was taken out, diluted with methanol to 50 mL in a measuring flask, and then 10 μL of the resultant solution was analyzed by HPLC.

The HPLC analysis was carried out under the following conditions.
Column: Reverse phase column "Develosil (Registered Trademark)
C-30-UG-5" (4.6 mmi.d.×250 mm)
Mobile phase: A . . . $H_2O$ (0.1% trifluoroacetic acid (TFA)),
  B . . . Acetonitrile (0.1% TFA)
Flow velocity: 1 mL/min
Injection: 10 μL
Detection: 254 nm
Gradient (% by capacity): From 80% A/20% B to 20% A/80% B for 30 minutes,
From 20% A/80% B to 100% B for 5 minutes, 100% B for 10 minutes (all straight line)

The compound eluted at the elution time of about 16.00 to 17.00 minutes under the HPLC conditions above was isolated by fractionation HPLC, and then dried by a usual method. Then, 129 mg of a brown powdery substance was obtained, and was named UHA1028.

Subsequently, the molecular weight of the UHA1028 was measured by a High Resolution Electron Ionization-Mass Spectrometry. Then, the measured value was 408.4436 and the following molecular formula was obtained from the comparison with the theoretical value.
Theoretical value $C_{24}H_{24}O_6$ ($M^+$): 408.4438
Molecular formula $C_{24}H_{24}O_6$ Next, the UHA1028 was subjected to nuclear magnetic resonance (NMR) measurement, and then it was confirmed from the analysis of $^1H$-NMR, 13C-NMR, and various two-dimensional NMR data that the UHA1028 has the structure represented by Formula (3).

Formula (3)

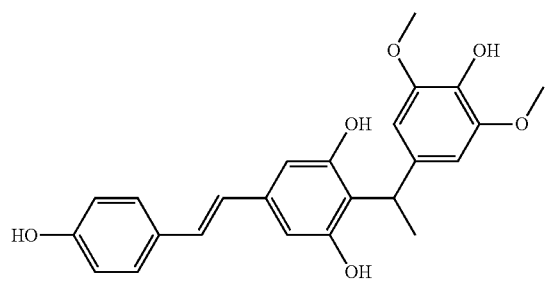

The present inventors confirmed so far that the UHA1028 has an anti-cancer action (Patent Literature 3), a sirtuin expression promotion action in human vascular endothelial cells (Japanese Patent Application No. 2011-118367), an adiponectin production promotion action in mature adipocytes (Japanese Patent Application No. 2011-145331), a lipoprotein lipase promotion action in mature adipocytes (Japanese Patent Application No. 2011-186054), and a differential inhibition action to mature adipocytes of preadipocytes (Japanese Patent Application No. 2012-240364), and the like but did not confirm the effect of the differentiation induction to brown-like adipocytes from white adipocytes and the effect has not generally known yet.

Example 2

Verification of Expression of Indicator Gene of Differentiation Induction Action to Brown-Like Adipocytes of White Adipocytes of UHA1028

In order to evaluate the differentiation induction action to brown-like adipocytes of white adipocytes, the evaluation was carried out using 3T3-L1 cells (mouse-derived preadipocytes). The 3T3-L1 preadipocytes are usually differentiated to white adipocytes through a differentiation induction process to be matured. However, by the differentiation induction to brown-like adipocytes, an expression of Cidea gene, an increase in the expression amount of Cox7a1 gene expressed in mitochondria, an increase in the expression amount of cytochrome c oxidase protein specifically expressed in mitochondria, and an expression enhancement of UCP1 gene, which are hardly observed in white adipocytes, are observed. Then, the differentiation induction to brown-like adipocytes of white adipocytes was confirmed based on the expression amount of each gene of Cidea, Cox7a1, and UCP1.

For samples, two substances of resveratrol and UHA1028 were used. Since the action of the differentiation induction to brown-like adipocytes was not observed in sinapic acid, sinapic acid was not used as a comparison target. Each sample was dissolved in dimethylsulfoxide (DMSO, manufactured by Wako Pure Chemical Industries, Ltd.) with a concentration of 4 mM and 2 mM to be used for a test.

Culture was carried out using "Dulbecco's modified Eagle medium" (DMEM, Product name, manufactured by Sigma-Aldrich Corporation) containing 10% "Foetal Bovine Serum" (FBS, manufactured by Biological industries), 1% "Antibiotic-Antimycotic", and GIBCO (manufactured by Life Technology Corporation). Adipocytes to be used for the test were prepared in accordance with a usual method.

The test was carried out as follows. 2 mL of 3T3-L1 cells were sowed with a concentration of $5 \times 10^4$ cells/mL in a 6 well dish for cell culture (manufactured by Japan Becton, Dickinson and Company), and then cultured under the conditions of 37° C. and 5% $CO_2$ for 24 hours. 24 hours later, the DMEM culture medium was exchanged to a DMEM culture medium which was adjusted in such a manner that the final concentration of the UHA1028 was 10 μM or the final concentration of the resveratrol was 20 μM, culture was continued in such a manner that the cells were confluent to 100%, and then culture was further carried out for 48 hours. Next, the culture medium was exchanged to a culture medium in which 10 μL of each sample (Final concentration of 20 μM and 10 μM) was added to 2 mL DMEM for differentiation, to which 1% of insulin, 0.5% of dexamethasone, and 0.1% of isobutylmethylxanthine were added, attached to "AdipoInducer Reagent" (Product name, manufactured by Takara Bio, Inc.), and then differentiation induction was carried out under the conditions of 37° C. and 5% $CO_2$ for 48 hours. After the differentiation induction for 48 hours, the culture medium was exchanged to 2 mL of DMEM for maintaining culture to which 1% of insulin was added, and then culture was further carried out for one week for maturing adipocytes. One to which 0.5% of only DMSO which is a solvent was added was used as a control.

After the end of the culture, the total amount RNA was extracted from the cells using an RNA extraction kit (Product name: NucleoSpin (Registered Trademark) RNA II, manufactured by Takara Bio, Inc.) and refined. The obtained RNA was subjected to a reverse transcription reaction in accordance with the operation manual of a reverse transcription reagent for two-step real-time RT-PCR (Product name: Prime Script (Registered Trademark) RT Master Mix, manufactured by Takara Bio, Inc.).

More specifically, 4 μL of 5× (Primescript RT Master Mix) and 1 μg of the total amount RNA were mixed, and the total amount was set to 20 μL by RNase Free $dH_2O$. The reverse transcription reaction was performed in accordance with a program in which one cycle is "37° C.×15 minutes→85° C.×5 seconds" using a thermal cycler for PCR (Product name: GeneAmp (Registered Trademark) PCR System 9700, manufactured by Applied Biosystem, Inc.). A diluent obtained by diluting a reverse transcription reaction liquid 10 times with a diluted reagent for real-time RT-PCR (Product name: EASY Dilution, manufactured by Takara Bio, Inc.) was used for the real-time RT-PCR analysis.

The real-time RT-PCR analysis was carried out in accordance with a usual method. For the analysis, "ECO Realtime RT-PCR system" (Product name, manufactured by Illumina, Inc.) was used. For a primer, a Cidea forward primer (Primer ID: MA104629-F), a Cidea reverse primer (Primer ID: MA104629-R), a Cox7a1 forward primer (Primer ID: MA106801-F), a Cox7a1 reverse primer (Primer ID: MA106801-R), a UCP1 forward primer (Primer ID: MA027561-F), and a UCP1 reverse primer (Primer ID: MA027561-R) were used. As the internal standard of intracellular genes, β-actin was used. As the primer thereof, an ACTB forward primer (Primer ID: MA050368-F) and an ACTB reverse primer (Primer ID: MA050368-R) (The eight kinds of primers above are all manufactured by Takara Bio, Inc.) were used.

For the reaction, a real-time RT-PCR reagent (Product name: SYBR(Registered Trademark) Premix EX taqII (Tli RNaseH Plus), manufactured by Takara Bio, Inc.) was used. A reaction liquid was obtained by mixing 5 μL of 2× (SYBR Premix EX taq II (Tli RNaseH Plus)), 0.08 μL of a forward primer (50 μM), 0.08 μL of a reverse primer (50 μM), 2 μL of a reverse transcription reaction liquid, and 2.84 μL of $dH_2O$ (Total amount of 10 μL) in a 48 well PCR plate (manufactured by Illumina, Inc.). The PCR reaction was performed in accordance with a program of {"95° C.×30 seconds→"95° C.×15 seconds→60° C.×1 minute"×40 cycles→95° C.×15 seconds→55° C.×15 seconds→95° C.×15 seconds}.

The relative value of the gene expression amount of each gene of Cidea, Cox7a1, and UCP1 was calculated from the Ct values (Threshold Cycle: Number of cycles reaching fixed amplification amount (threshold value) of β-actin, Cidea, Cox7a1, and UCP1 in the obtained cells. The results are shown in FIG. 1.

As a result, it was found that, as compared with the case of adding resveratrol, the gene expression amount of the Cidea which is a marker gene of the brown-like adipocytes significantly increased when adding the UHA1028. Furthermore, it was clarified that the expression amount of the Cox7a1 which is a mitochondria marker gene significantly increased. Moreover, it was clarified that the expression amount of the UCP1 gene also significantly increased. More specifically, it was shown that the possibility of having an extremely strong differentiation induction action to brown-like adipocytes of white adipocytes is high as compared with resveratrol.

Example 3

Verification of Expression of Indicator Protein of Differentiation Induction Action to Brown-Like Adipocytes of White Adipocytes of UHA1028

In order to evaluate the differentiation induction action to brown-like adipocytes of white adipocytes, the evaluation was carried out using 3T3-L1 cells (mouse-derived preadipocytes). The 3T3-L1 preadipocytes are usually differentiated to white adipocytes through a differentiation induction process to be matured. However, by the differentiation induction to brown-like adipocytes, an increase in the expression amount of cytochrome c oxidase protein specifically expressed in mitochondria is observed. Then, the differentiation induction to brown-like adipocytes of white adipocytes was confirmed based on the expression amount of the CO1 protein.

Culture of cells was carried out by the same method as that of Example 2 using the same samples and cells as those in Example 2. After the end of the culture, 400 μL of RIPA buffer (manufactured by Sigma-Aldrich Corporation) was added to the cells, and protein was extracted. After the extraction, the protein concentration was measured using a BCA protein assay kit (manufactured by Thermo Fisher Scientific K.K.).

As protein samples for SDS-polyacrylamide electrophoresis, one obtained by adding one-fifth amount of Laemmli sample buffer (10% sodium dodecyl sulfate, 100 mM dithiothreitol, 30% glycerol, 50 mM Tris-HCl, pH 6.8) to 10 mug equivalent protein, and then denaturing the mixture by heating at 95° C. for 5 minutes was used. For a gel, "Mini-protean TGX Any kD Gel" (manufactured by Bio-Rad Laboratories Inc.) was used.

The total amount of the denatured protein sample was used for the gel, and then subjected to electrophoresis at 200 V for 30 minutes.

After the electrophoresis, the proteins are transferred to PVDF membranes (manufactured by EMD Millipore) by a semidry blotting device "TRANS-BLOT S-D SEMI-DRY TRANSFER CELL" (Product name, manufactured by Bio-Rad Laboratories Inc.), and then blotting was carried out by Immunoblock (manufactured by DS Pharma Biomedical Co., Ltd.). Then, with respect to CO1, the detection of intracellular mitochondria was carried out by an antibody reaction using "mitochondrial Complex IV subunit1 Mouse monoclonal Antibody" (primary antibody, manufactured by abcam plc.) and "Anti-Mouse IgG, HRP-linked Antibody" (secondary antibody, manufactured by Cell Signaling Technology Japan, K.K.). The band strength of the detected band was calculated using an image analysis software "Image J". These results are shown in FIG. 2.

Figure 2:
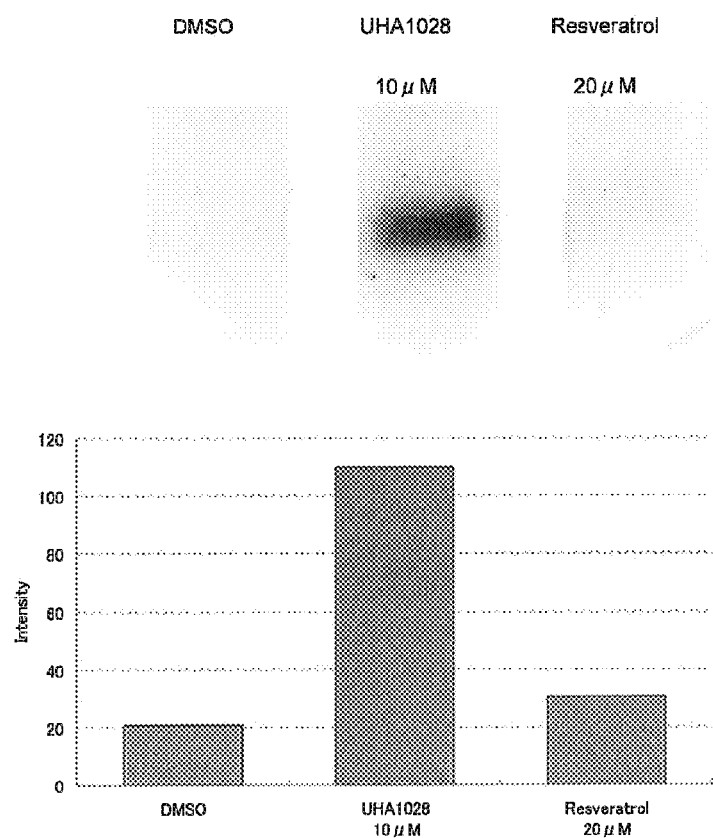
FIG. 2 is a graph showing the expression amount of cytochrome c oxidase subunit I protein (CO1) reflecting the amount of mitochondrias in adipocytes after differentiation induction carried out in Example 3 and shows the Western blot analysis results.

It is clarified from FIG. 2 that, with respect to the mitochondria marker protein expressed in mature adipocytes, the number of cells to which the UHA1028 was added was significantly large as compared in the case of adding DMSO and resveratrol and the expression level of mitochondria in the cells is high.

It was shown from the results of Examples 2 and 3 that, by adding the UHA1028, the amount of mitochondria in the cells significantly increased and the differentiation to brown-like adipocytes from white adipocytes was notably induced as compared with resveratrol, and therefore the UHA1028 is a compound excellent in the differentiation induction effect to brown-like adipocytes.

Example 4

Preparation of UHA1028-Containing Extract

A mixed solution (pH=3.5) prepared by adding 10 g of grape extracted essence powder (resveratrol containing material), 15 g of 7-times concentrated apple fruit juice (sinapic acid containing material), 10 mL of ethanol, and 10 mL of mineral water was heated at 130° C. for 180 minutes in an autoclave. The obtained reaction solution was dried and solidified under reduced pressure, thereby obtaining 20 g of a UHA1028-containing extract. In 20 g of the obtained UHA1028-containing extract, 0.056 g of the UHA1028 was contained as measured in the same manner as in Example 1.

Example 5

UHA1028-Containing Food 1 g of the UHA1028-containing extract obtained in Example 4 was dissolved in 100 mL of ethanol beforehand, 500 g of sugar and 400 g of starch syrup were mixed and dissolved therein, 100 g of fresh cream, 20 g of butter, 70 g of condensed milk, and 1.0 g of emulsifier were mixed therewith, the pressure was reduced by −550 mmHg in a vacuum pan, and then the resultant mixture was concentrated under the conditions of 115° C., thereby obtaining a milk hard candy with a moisture value of 3.0% by weight. It is a matter of course that the milk hard candy is easy to eat as a confectionery and also can be utilized as a functional food which is expected to reduce the differentiation to mature adipocytes from preadipocytes to prevent obesity.

Example 6

UHA1028-Containing Pharmaceutical Drug

The UHA1028-containing extract obtained in Example 4 was dissolved in ethanol, and then the solution was added and adsorbed to microcrystalline cellulose, followed by drying under reduced pressure. A tablet was obtained using the adsorbed substance in accordance with a usual method. The formulation is as follows: 10 parts by weight of the UHA1028-containing extract, 23 parts by weight of cornstarch, 12 parts by weight of lactose, 8 parts by weight of carboxymethyl cellulose, 32 parts by weight of microcrystalline cellulose, 4 parts by weight of polyvinyl pyrrolidone, 3 parts by weight of magnesium stearate, and 8 parts by weight of talc. This tablet can be effectively utilized as a pharmaceutical drug aiming at recovery from obesity.

Example 7

UHA1028-Containing Quasi Drug 1.2 g of the UHA1028-containing extract obtained in Example 4 was dissolved in 10 mL of ethanol, purified water in which 20 g of taurine, 0.12 g of vitamin B1 nitrate, 0.6 g of sodium benzoate, 4 g of citric acid, and 10 g of polyvinyl pyrrolidone were dissolved was mixed with the solution, and then the resultant mixture was diluted to 1000 mL with purified water in a measuring flask. The pH was adjusted to 3.2 using dilute hydrochloric acid. A glass bottle was filled up with 50 mL of 1000 mL of the obtained solution, and then sterilized by heating at 80° C. for 30 minutes, thereby completing a health drink which is a quasi drug. This health drink can be effectively utilized as a quasi drug not only for the purpose of nutrition but for the purpose of recovery from and prevention of obesity.

What is claimed is:
1. A differentiation inducer to brown-like adipocytes of white adipocytes which is a reaction product of hydroxystilbenes and sinapic acid, comprising:
    a compound represented by Formula (1) or a pharmacologically permissible salt thereof:

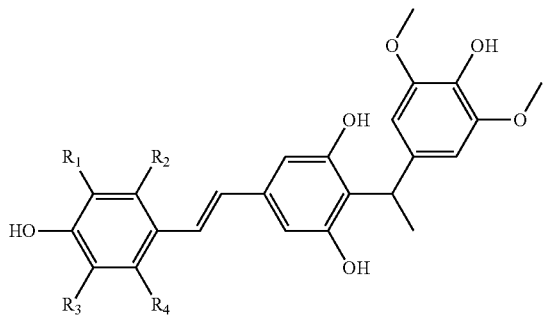

Formula (1)

wherein, in Formula (1), $R_1$ to $R_4$ represents a hydrogen atom, a hydroxy group, a saturated or unsaturated, linear or branched alkoxy group having 1 to 10 carbon atoms, or a saturated or unsaturated, linear or branched alkyl group having 1 to 10 carbon atoms, and
$R_1$ to $R_4$ each may be the same or different.

* * * * *